(12) United States Patent
LaCourt et al.

(10) Patent No.: US 7,402,282 B2
(45) Date of Patent: Jul. 22, 2008

(54) AUXILIARY SAMPLE SUPPLY FOR A CLINICAL ANALYZER

(75) Inventors: Michael W. LaCourt, Spencerport, NY (US); James David Shaw, Hilton, NY (US); Michael Avdenko, Rochester, NY (US); Lee William David, Penfield, NY (US); Dale Robert Ryan, Fairport, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 12 days.

(21) Appl. No.: 09/910,399

(22) Filed: Jul. 20, 2001

(65) Prior Publication Data

US 2003/0026733 A1 Feb. 6, 2003

(51) Int. Cl.
*G01N 35/02* (2006.01)
*G01N 35/04* (2006.01)

(52) U.S. Cl. .............................. 422/64; 422/65; 422/67; 422/100

(58) Field of Classification Search ............ 422/64, 422/65, 66, 67, 100
See application file for complete search history.

(56) References Cited

U.S. PATENT DOCUMENTS

| | | | |
|---|---|---|---|
| 4,340,390 A | 7/1982 | Collins et al. | |
| 4,353,868 A | 10/1982 | Joslin et al. | |
| 4,420,254 A | 12/1983 | Smeaton | |
| 4,847,050 A | 7/1989 | Jenkins et al. | |
| 4,903,708 A | 2/1990 | Saint-Amand | |
| 5,221,311 A | 6/1993 | Rising et al. | |
| 5,254,312 A | 10/1993 | Staebler et al. | |
| 5,260,028 A | 11/1993 | Astle | |
| 5,364,598 A | 11/1994 | Oxley | |
| 5,411,065 A * | 5/1995 | Meador et al. | 141/1 |
| 5,415,839 A | 5/1995 | Zaun et al. | |
| 5,549,141 A * | 8/1996 | Meador et al. | 141/1 |
| 5,645,801 A | 7/1997 | Bouma et al. | |
| 5,658,723 A | 8/1997 | Oberhardt | |
| 5,807,522 A | 9/1998 | Brown et al. | |
| 5,846,492 A * | 12/1998 | Jacobs et al. | 422/67 |
| 5,958,341 A | 9/1999 | Chu | |
| 5,996,309 A | 12/1999 | Focke et al. | |
| 6,068,978 A | 5/2000 | Zaun et al. | |
| 6,086,824 A | 7/2000 | Fanning et al. | |
| 6,100,026 A | 8/2000 | Nova et al. | |
| 6,180,061 B1 | 1/2001 | Bogen et al. | |
| 6,195,158 B1 | 2/2001 | Cadell et al. | |
| 6,197,494 B1 | 3/2001 | Oberhardt | |
| 6,267,927 B1 * | 7/2001 | Pomar Longedo et al. | 422/65 |
| 6,268,910 B1 | 7/2001 | Samsoondar et al. | |
| 6,797,518 B1 | 9/2004 | Jacobs et al. | |
| 2002/0110487 A1 | 8/2002 | Samsoondar | |
| 2005/0054112 A1 | 3/2005 | Jacobs et al. | |

FOREIGN PATENT DOCUMENTS

| | | |
|---|---|---|
| EP | 0 571 032 A1 | 11/1993 |
| EP | 1 052 513 A1 | 11/2000 |

(Continued)

*Primary Examiner*—Jan M Ludlow

(57) ABSTRACT

A sample handler includes a plurality of sealable metering tips, each of the tips, when sealed, containing a fluid volume of a test fluid and in which each of the sealed metering tips acts as an auxiliary sample supply container for use with at least one chemistry system of a clinical analyzer.

11 Claims, 9 Drawing Sheets

| | FOREIGN PATENT DOCUMENTS | | WO | 99/47261 | 9/1999 |
|---|---|---|---|---|---|
| EP | 1 186 893 A2 | 3/2002 | WO | 01/12329 A1 | 2/2001 |
| WO | WO 91/17446 | 11/1991 | | | |
| WO | WO9220778 | 11/1992 | * cited by examiner | | |

AUXILIARY SAMPLE SUPPLY FOR A CLINICAL ANALYZER

FIELD OF THE INVENTION

The invention relates to the field of analytical test sample measurement and more particularly to an auxiliary sample supply/buffer for a combinational clinical analyzer which effectively links at least two contained chemistry systems.

BACKGROUND OF THE INVENTION

In a so-called combinational clinical analyzers a dry chemistry system and a wet chemistry system, for example, can be provided within a contained housing.

Each of the above chemistry systems are somewhat unique in terms of their operation. For example, known "dry" chemistry systems typically include a sample supply which includes a number of sample containers, a metering/transport mechanism, and an incubator having a plurality of test read stations. A quantity of sample is aspirated into a metering tip using a proboscis or probe carried by a movable metering truck along a transport rail. A quantity of sample from the tip is then metered (dispensed) onto a dry slide element which is loaded into the incubator. The slide element is incubated and optical or other reads are taken for analyte detection.

A "wet" chemistry system on the other hand, utilizes a reaction vessel such as a cuvette, into which quantities of patient sample, at least one reagent fluid, and/or other fluids are combined for conducting an assay. The assay is also incubated and tests are conducted for analyte detection. The "wet" chemistry system also includes a metering mechanism to transport patient sample fluid from the sample supply to the reaction vessel.

A number of known clinical analyzers incorporate both wet and dry chemistry systems in a single apparatus. To date, however, there has been no attempt to improve the efficiency/throughput of such devices by effectively linking the chemistry systems of a combinational clinical analyzer together.

SUMMARY OF THE INVENTION

A primary object of the invention is to avoid the above-identified deficiencies of the prior art.

It is another primary object of the invention to provide means for linking at least two chemistry systems of a combinational clinical analyzer in a manner which improves overall throughput and efficiency.

Therefore and according to a preferred aspect of the invention, there is provided a sample, sample handling means for retaining a plurality of sample fluids; and a plurality of metering tips retained by said sample handling means, each of said metering tips having a sealable dispense end which after sealing retains a volume of test fluid, each of said sealed metering tips serving as a sample container for use with at least one chemistry system of a clinical analyzer.

The sample handling means includes a plurality of sealed tip receiving stations, each of the sealed tip receiving stations being sized to retain a sealed metering tip. The handler also preferably includes tip supply means for supplying a plurality of unsealed metering tips.

According to a preferred embodiment, the sample handling means and the tip supply means include a pair of concentric ring members, each of the ring members including a plurality of tip receiving stations for receiving sealed and unsealed metering tips which can be rotatably driven about a common axis. More preferably, each of the ring members are capable of being independently driven bidirectionally about the common rotational axis.

The sample handler further includes sealing means, preferably a heated element such as an anvil or other suitable apparatus which is used to individually seal the metering tips containing test fluid. Following sealing, the tip is stripped and placed into a tip receiving station of the handler. The sealed tip acts as a sample container and therefore can be used with, for example, smaller metering tips which can fit within the confines of the tip and aspirate sample as needed in conjunction with a chemistry system of the analyzer.

The sample contents of the sealed metering tips can also be tested while retained using certain test apparatus, such as a spectrophotometer to evaluate the integrity of the contained test fluid.

According to yet another preferred aspect of the invention, there is provided a clinical analyzer for testing patient fluids, said analyzer comprising a housing; at least one chemistry system retained within the housing; first sample handling means for handling a plurality of first patient sample containers; and second sample handling means for retaining a plurality of second patient sample containers, each of said sample handling means being interconnected with at least one said chemistry system.

Preferably, the analyzer includes first conveying means for conveying a quantity of sample from the first sample handling means to at least one chemistry system. The first conveying means includes at least one metering tip, the tip being sized for aspirating a quantity of sample from a first sample container through a dispense end.

The second sample handling means comprises at least one metering tip having aspirated sample from the first sample container and which has been sealed prior to moving the tip to the second sample handling means.

According to still another preferred aspect of the invention, there is provided a buffer for interconnecting respective chemistry systems of a combinational clinical analyzer having a primary sample supply, said buffer comprising sealed tip retaining means for retaining a plurality of sealable metering tips, each of said tips after sealing containing a quantity of sample aspirated from said primary sample supply, said buffer acting as an auxiliary sample supply in connection with at least one of said chemistry systems.

According to a preferred embodiment, the buffer includes sealing means for sealing the dispense end of each of the metering tips containing aspirated sample. More preferably, the sealing means is a heated element, such as an anvil for fusing the dispense end of a sample containing metering tip.

The buffer also includes unsealed tip retaining means for retaining a supply of unsealed metering tips which are connected to first conveying means of the analyzer linking the unsealed metering tip supply with the primary sample supply.

The sealed tip retaining means and the unsealed tip retaining means are preferably concentric ring members which are independently driven about a common axis of rotation, each of the ring members including a plurality of tip retaining stations. More preferably, the ring members can be driven bidirectionally to expedite getting either a sealed tip or an unsealed tip to a specified location.

According to yet another preferred aspect of the invention, there is provided a method for coordinating the use of a combinational clinical analyzer, said method including the steps of:

introducing a quantity of sample fluid from at least one first sample container into at least one metering tip;

sealing the dispense end of said at least one metering tip; and utilizing said at least one metering tip as a second sample container for use with at least one chemistry system of the analyzer.

Preferably, the introducing step includes the step of aspirating a quantity of sample fluid from a primary sample supply into at least one metering tip in which the primary sample supply includes a plurality of primary sample containers and in which the at least one metering tip is used as a secondary sample container.

According to a preferred embodiment, the analyzer includes at least one dry chemistry system and at least one dry chemistry system wherein the sealed metering tip containing aspirated sample fluid is used in conjunction with at least the wet chemistry system.

In the preferred embodiment, a quantity of sample fluid is dispensed for use with the dry chemistry system of the analyzer prior to the sealing step.

Preferably, a plurality of sealed metering tips are loaded into a rotatable assembly in alignment with a metering mechanism of at least the wet chemistry system. A second metering tip which is smaller than a sealed metering tip is used to aspirate sample fluid from the sealed metering tip for conducting a wet assay or dilution in conjunction with the wet chemistry system of the analyzer or for conducting a dilution or dry assay in conjunction with the dry chemistry system.

According to this invention, the sample handler preferably acts as a buffer between for example, a wet chemistry and a dry chemistry analysis system of a clinical analyzer, and allows each chemistry system to operate asynchronously in order to increase the overall test throughput of the analyzer. As such, an auxiliary random access sample handler is provided to support, for example, the processing of wet assays. Aliquots of primary samples are stored in the sealed metering tips contained within the buffer to allow a number of different functions to be performed.

Preferably, the buffer includes a test read station in which all samples being assayed by each of the chemistry systems of the analyzer can be monitored for conditions such as hemolysis, sample volume, lipemia, icterus, and others.

In addition, the buffer allows interaction between either or multiple chemistry systems of a combinational analyzer. For example, the buffer can functionally perform as the sample supply for the wet chemistry system or portion of the analyzer while also using sample to create diluted samples for dry assays. Because the buffer performs as a sample handler, the buffer also permits reflex testing of both dry and wet assays without requiring a volume of sample from the primary sample handler of the analyzer.

A feature is that the herein described buffer permits both the wet and dry sides of a combinational analyzer to be run independently of each other and in which each chemistry system operates from its own sample handler; that is, the dry chemistry system utilizes the primary sample handler while the wet chemistry system utilizes the herein described auxiliary sample handler.

A very advantageous feature of the herein described invention is the use of a disposable metering tip as an aliquot container. This is accomplished by sealing the end of the tip (with the required amount of fluid to support both dilutions and wet assays) while the tip is still attached to the proboscis. The tip sealing apparatus is preferably incorporated or integrated into the aliquot buffer design in which sealing is performed by pressing the dispense end of the tip into a heated anvil or other element while the tip is still supported by the proboscis. The dispense end of the tip is thereby to congeal or coagulate, preventing fluid from leaking out of the bottom and producing a fluid container. A small bubble of air is aspirated prior to sealing the dispense end of the tip in order to evacuate fluid from the end of the tip to ensure both a reliable seal and to limit the temperature rise of the fluid. Preferably, a tip stripping assembly is incorporated into the cover of the aliquot buffer.

An empty sample container supply position located on the inner rotor is positioned beneath the tip stripping assembly in order to receive the sealed tip containing the sample volume. Hence, a sample aliquot is created without the use of additional consumable.

The remaining open top end of the sealed metering tip becomes a port for accessing the sample via a fluid aspirating device, such as another metering tip of the same or similar dimensions or a smaller micro tip which is sized to be fitted within the confines of a sealed metering tip. Therefore, the sealed metering tip is used as a sample supply in connection with at least one chemistry system or the like. Preferably, a sensor determines that a sample container supply position is empty before a sealed tip is dropped into the sample handler, the sensor further determining whether the metering tip has been successfully positioned in the handler.

Once the sample container has been loaded into the auxiliary sample handler, the scheduling computer of the clinical analyzer moves the sample retained within the tip to specific aspiration station[s] for conducting assays, as well as a sample integrity read station. The sample integrity read station is used to perform a light transmission/absorption or other optical test on the sample. By providing the read station within the sample handler, a read can be made on the fluid contents of a sealed sample container without interfering with the throughput of the analyzer. The sample handler also includes a dump station to eliminate/dispose of the sealed metering tips after any assays (testing) are completed.

The auxiliary sample handler preferably includes a ring member which is capable of supporting a plurality of sealed metering tips, the ring being rotatable about a primary axis. Preferably, a drive mechanism is provided capable of driving the ring member bidirectionally in order to selectively expedite moving a sample of interest as needed.

The sample handler may include a thermistor and other thermal control device, such as peatier elements or the like, which enables the temperature of the sample containers to be tightly controlled while the samples are retained.

According to at least one described embodiment, the sample integrity read station includes a tip positioning or lift mechanism which specifically locates the retained sealed metering tips relative to an optical testing apparatus, such as a spectrophotometer.

An advantage provided by the present invention is that an auxiliary sample handler is provided which can be used in conjunction with a combinational analyzer having two or more chemistry systems. The auxiliary sample handler provided improved efficiency and increased throughput.

A further advantage provided by the present invention is that the wet chemistry system does not need to rely upon the primary sample supply and primary metering mechanism. That is, each chemistry system of the analyzer can be operated asynchronously with respect to the other.

Still another advantage of the present invention is the use of sealed metering tips as a sample container for a contained chemistry system of an analyzer. The sealed tips retain a sufficient volume of patient fluid and since the sealed tips are disposable, there is no need for washing operations for the sealed tips after use.

The cover of the buffer/sample handler of the present invention can also be used to detect operator access, a safety feature to insure the samples are not handled while in the buffer. In addition, the cover also provides evaporation control of the contained samples.

These and other objects, features, and advantages will become apparent from the following Detailed Description which should be read in conjunction with the accompanying drawings.

DETAILED DESCRIPTION

The following description relates to an auxiliary sample handling apparatus which is used in conjunction with a specific combinational (ie., wet/dry) clinical analyzer that is used for the testing of biological samples, such as whole blood serum or plasma and more preferably human patient samples.

By "combinational" it is meant that the analyzer includes at least two chemistry systems which can encompass any combination of "dry" and/or "wet" chemistry systems. In brief and in a typical "dry" chemistry system, a patient sample and/or other fluids are aspirated from a fluid supply and deposited onto a dry slide element such as those described in U.S. Pat. No. 3,992,158 to Przyblyowicz et al. The dry slide element is incubated and the amount or presence of at least one analyte in the sample metered onto the element is determined, such as through use of an electrometer, reflectometer or other suitable testing device.

A "wet" chemistry system for purposes of the description which follows includes a reaction vessel which receives predetermined volumetric quantities of sample, reagent, and other fluids which are appropriately metered into the reaction vessel in order to perform an assay(s). The assay is incubated as the fluids are added to the assay(s) and specific analysis is performed, such as through luminescence, light transmissivity, photon detection, and the like using suitable testing apparatus.

Several other terms are used throughout the discussion including the terms "metering tips" and "micro-tips". For purposes of this description, a metering tip refers to a fluid aspirating/dispensing member which can be attached to a proboscis as used in a metering mechanism. The tip includes an open top end and a bottom dispense end and is capable of retaining a volumetric quantity of fluid. Metering tips in and of themselves are repletely well known in the field. A "micro-tip" for purposes of this discussion refers to a metering tip which fits the definitional requirements set forth above. In addition, this tip is sized to retain a smaller (micro) volume of fluid. Moreover and essential to the discussion which follows, the micro-tip can be fitted within the confines of the metering tip for advantages which will be apparent below.

The analyzer which is described herein is a combinational analyzer having a single "dry" chemistry system and a single "wet" chemistry system. It will be readily understood from the discussion which follows, however, that several variations and modifications are possible which embody the essential concepts of the present invention. For example, the analyzer can include a pair of dry chemistry systems.

Figure 1:
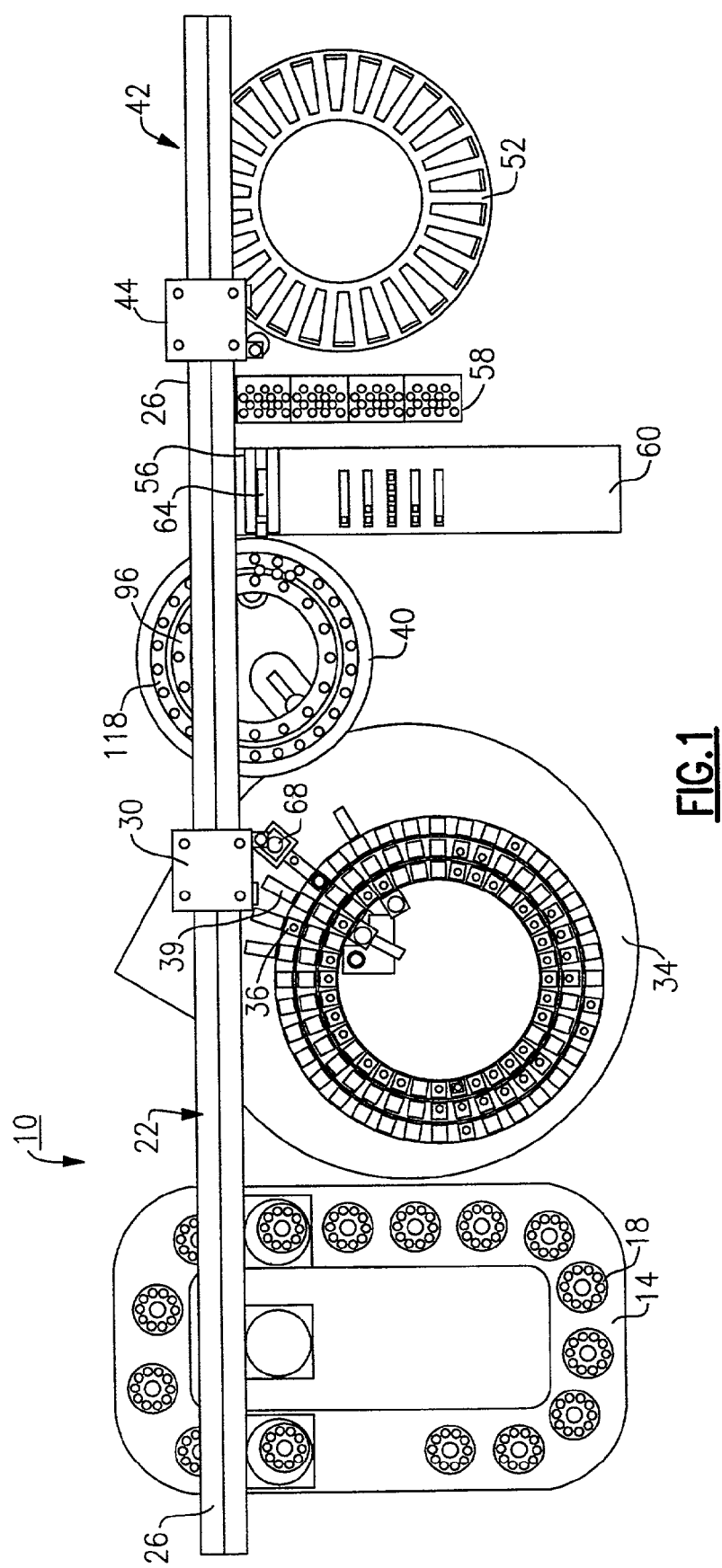
FIG. 1 is an operational block diagram of a combinational wet/dry clinical analyzer including an auxiliary sample handler made in accordance with a preferred embodiment of the invention.
Figure 2:
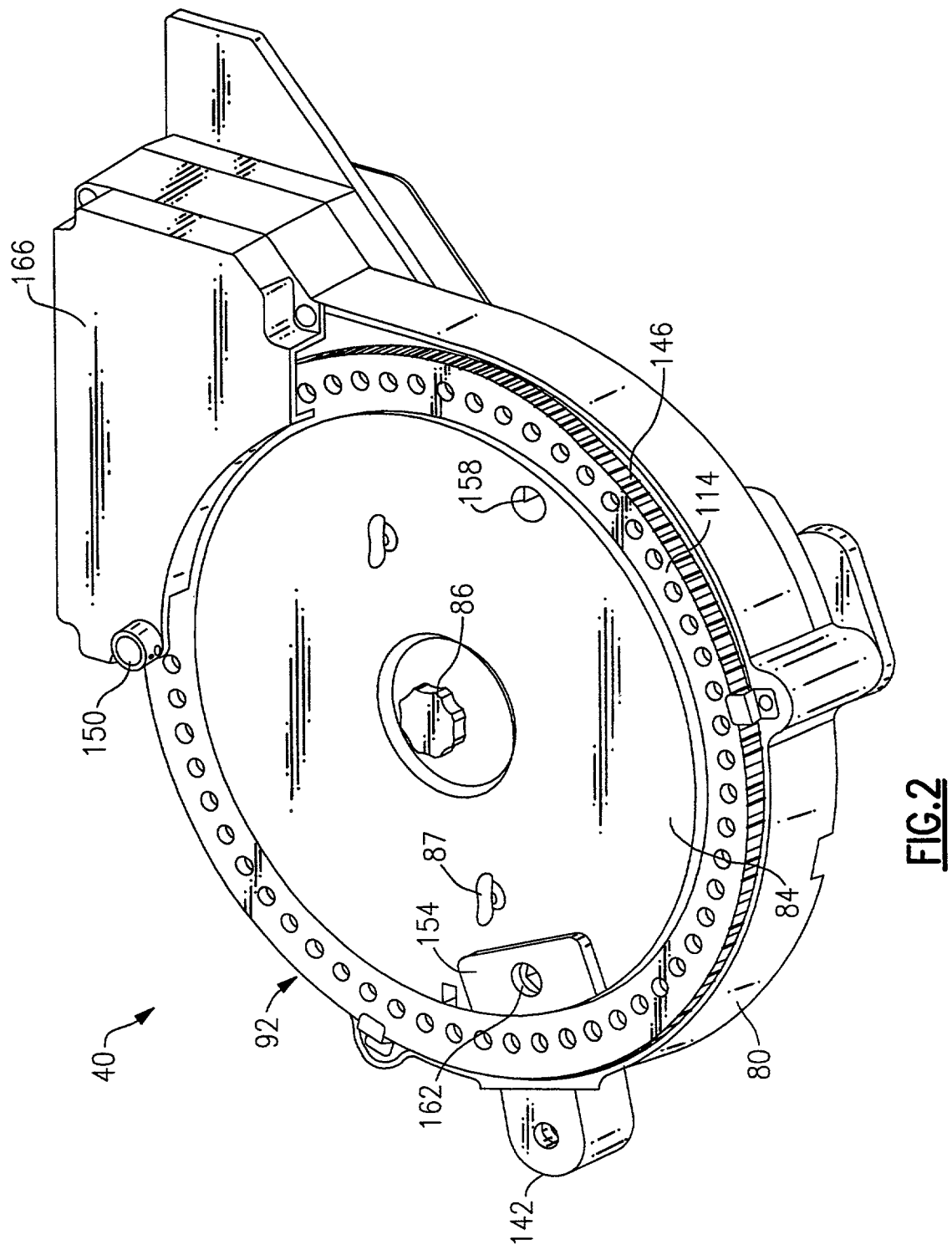
FIG. 2 is a top perspective view of the auxiliary sample handler of FIG. 1.

Referring to FIG. 1, there is shown an automated combinational clinical analyzer 10 having a number of component systems which are briefly discussed to provide adequate background for the invention. The analyzer 10 includes a primary sample handler 14 that retains a plurality of primary sample containers 18, a primary metering mechanism 22 which includes a metering transport rail 26 and a metering truck 30 which is movable along the transport rail between a number of stations. Among the stations disposed along the travel path of the metering mechanism 22 are a metering station 68 for a first incubator assembly 34. At the metering station 68, a quantity of sample can be deposited onto a dry slide element which is then shuttled into the incubator assembly 34. The incubator assembly 34 includes at least one read station including a testing device for correlated analyte detection, such as reflectometer (not shown) or an electrometer (not shown). The preceding components each comprise a dry chemistry system for the herein described automated combinational analyzer 10.

Still referring to FIG. 1, the analyzer 10 further includes a secondary metering mechanism 42 that includes a metering truck 44 which is also movable along the metering transport rail 26, a reagent wheel 52 which includes a plurality of containers of at least one reagent fluid, a second incubator assembly 56, a micro-tip supply 58, and a reaction vessel conveyor 60 which carries a plurality of reaction vessels 64. These components have merely been listed in this portion of the discussion. Details relating to their features will be additionally supplied in a later portion of the discussion. For purposes of this description, however, each of the above-noted components define a wet chemistry system for the herein described combinational analyzer 10.

Still referring to FIG. 1, an auxiliary sample handling apparatus 40 (hereinafter referred to as the auxiliary sample handler) is disposed in spaced relation between the first incubator assembly 34 of the dry chemistry system and the second incubator assembly 56 of the wet chemistry system of the above-described analyzer 10. The following discussion pertains to a specific description of the auxiliary sample handler 40 followed by the operational details of the sample handler in conjunction with the wet and dry chemistry systems of the herein described combinational analyzer 10.

First, and as shown in FIGS. 1-3 and 5, the auxiliary sample handler 40 includes a circular cylindrical housing 80 having a cover 84. The housing is defined by an interior sized for containing a number of retained components which include an inner rotor assembly 88 (not shown in FIG. 2) a pair of position sensors 126, 128, and a tip removing assembly 122.

Each of the above-noted components are attached to an interior facing surface of a bottom mounting plate 138 of the housing 80. In addition, an outer rotor assembly 92 is supported at the top of the housing 80, the outer rotor assembly being disposed outside the periphery of the cover 84.

A pair of stanchions 90 also extending from the interior facing surface of the mounting plate 138 assist in supporting the cover 84 which covers the inner rotor assembly 88. The cover 84 further includes a center handle 86, as well as a pair of opposing twist fasteners 87 which engage corresponding openings provided in the stanchions 90. The cover 84 also includes a tip stripping assembly 154 that is described in greater detail below. The following relates to a more detailed discussion of the inner and outer rotor assemblies 88, 92.

Figure 3:
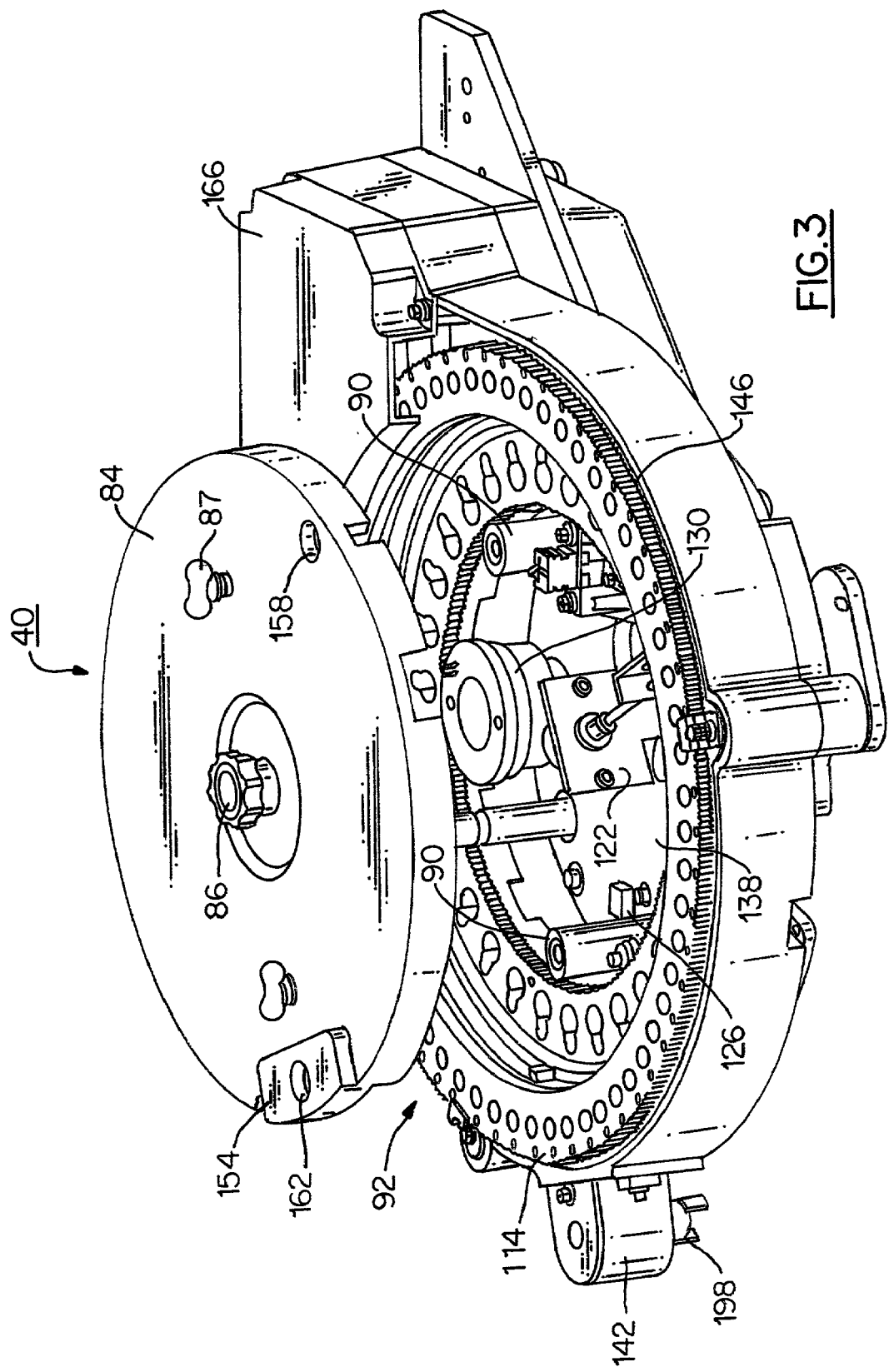
FIG. 3 is a partially exploded top perspective view of the auxiliary sample handler of FIGS. 1 and 2.
Figure 4:
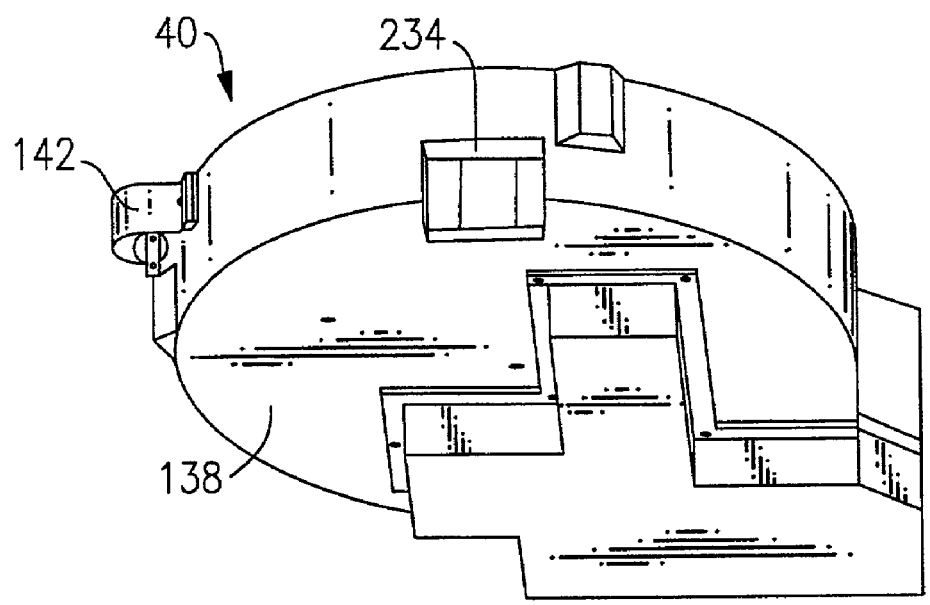
FIG. 4 is a bottom view of the auxiliary sample handler of FIGS. 1-3.
Figure 5:
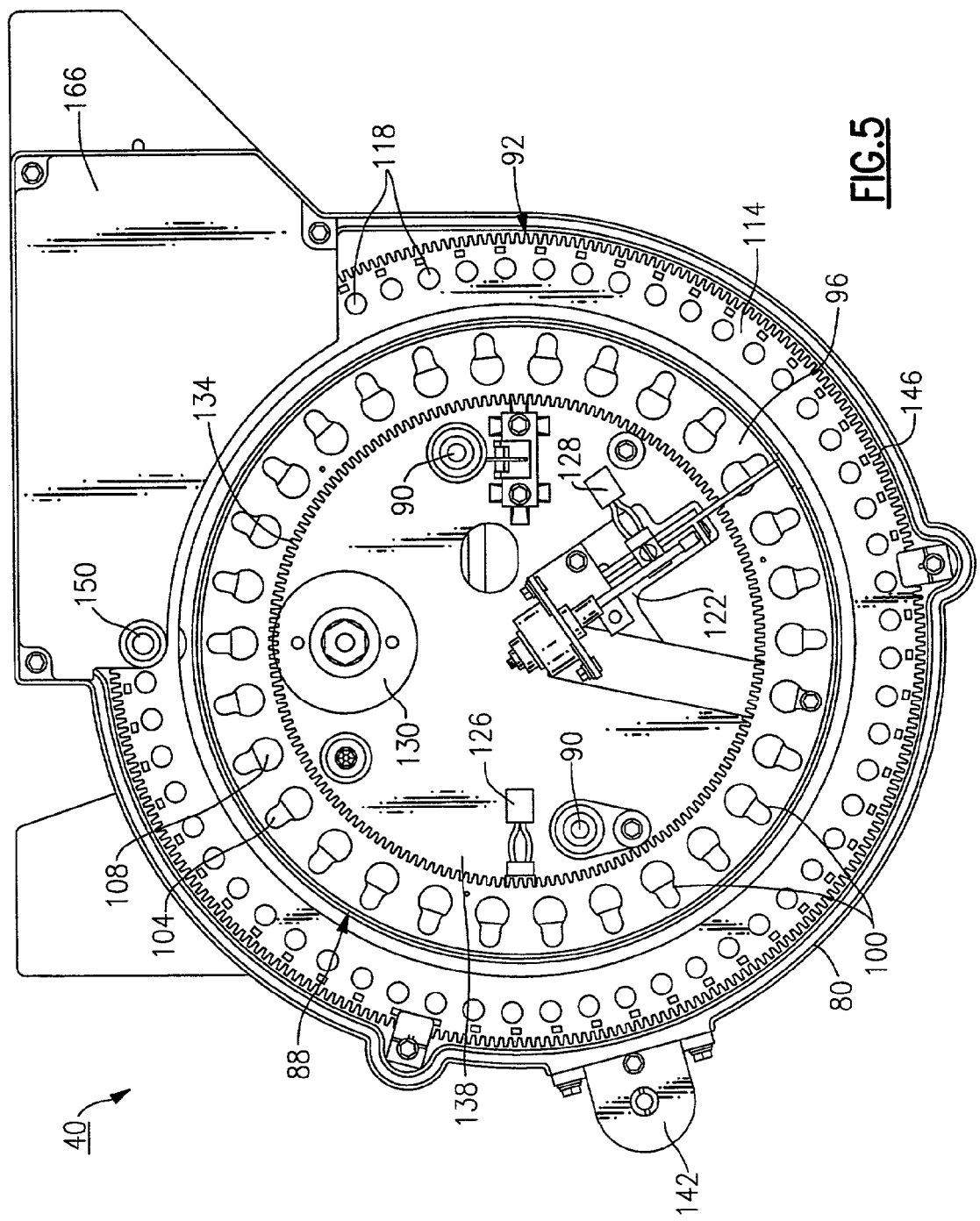
FIG. 5 is a top plan view of the auxiliary sample handler of FIGS. 1-4.
Figure 8:
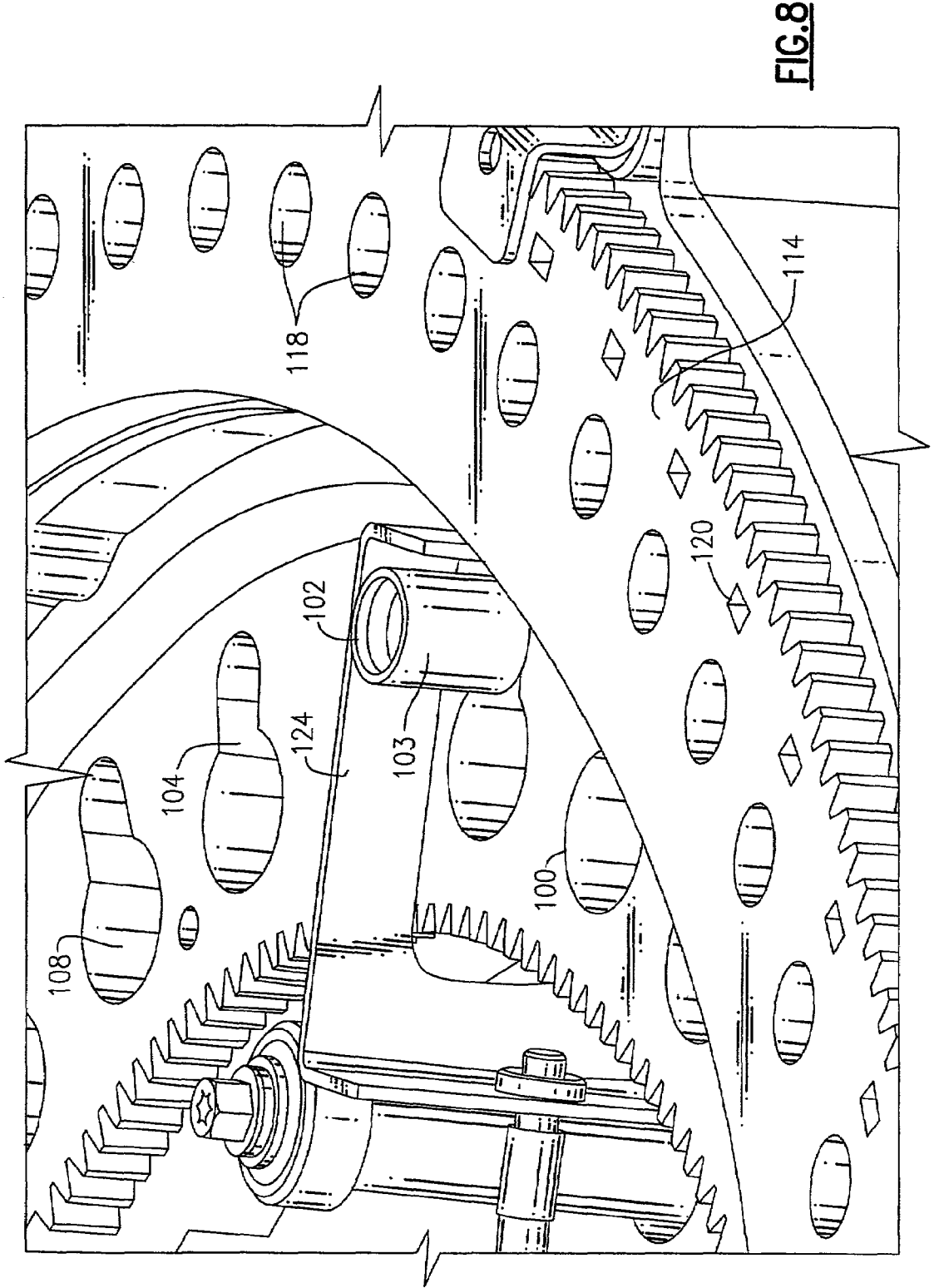
FIG. 8 is an enlarged partial top perspective view of the auxiliary sample handler of FIGS. 1-7 showing the removal of a sealed metering tip from the handler to a dump station.

Referring to FIGS. 3, 5, and 8, the inner rotor assembly 88 includes a rotatable circular ring member 96, which is rotatably driven about a center axis of rotation by means of a gear drive mechanism. The drive mechanism includes a motor having a rotating engagement portion 130 which extends above the interior facing surface of the mounting plate 138. A set of linear gear teeth 134 are provided on an inner edge of the ring member 96 which mesh with the engagement portion 130. The ring member 96 of the inner rotor assembly 88 further includes a plurality of sample container supply stations 100, each of the stations being circumferentially disposed about the periphery of the ring member. Each of the sample container supply stations 100 are defined by a slotted outer opening 104 which is linked to a radially adjacent and contiguous inner opening 108. The size of the inner opening 108 is much larger than that of the slotted outer opening 104 for reasons which will be become apparent below. According to this specific embodiment, (30) thirty sample container supply stations 100 are provided on the inner ring member 96, though it should be readily apparent that this parameter can be easily varied.

Referring now to FIGS. 2, 3, 5, and 8, and as noted above, the outer rotor assembly 92 of the auxiliary sample handler 40 extends outside the periphery of the cover 84. This assembly is comprised of a circular support ring 114 having a plurality of circular circumferentially disposed tip supply stations 118 which are equally spaced about the periphery of the ring. Like the inner rotor assembly 88, a gear drive mechanism is used to rotatably drive the ring. A set of linear gear teeth 146 provided on an outer edge of the support ring 114 are engaged by the engagement portion (not shown) of a motor (not shown) to cause rotation of the support ring 114. It should be pointed out that the above described gear drive mechanisms are exemplary. That is, other drive mechanisms can be employed to cause rotational movement of either the support ring 114 or the ring member 96.

The support ring 114 and the ring member 96 of the outer rotor assembly 92 and inner rotor assembly 88, respectively, are concentric, the rotating components of each assembly being independently driven by their respective gear drive mechanisms about a common axis of rotation.

According to this embodiment, the support ring 114 of the outer rotor assembly 92 further includes a series of circumferentially spaced slots 120, FIG. 8, disposed on an outer periphery of the ring for aiding in the initial angular positioning of the ring during assembly.

Figure 9:
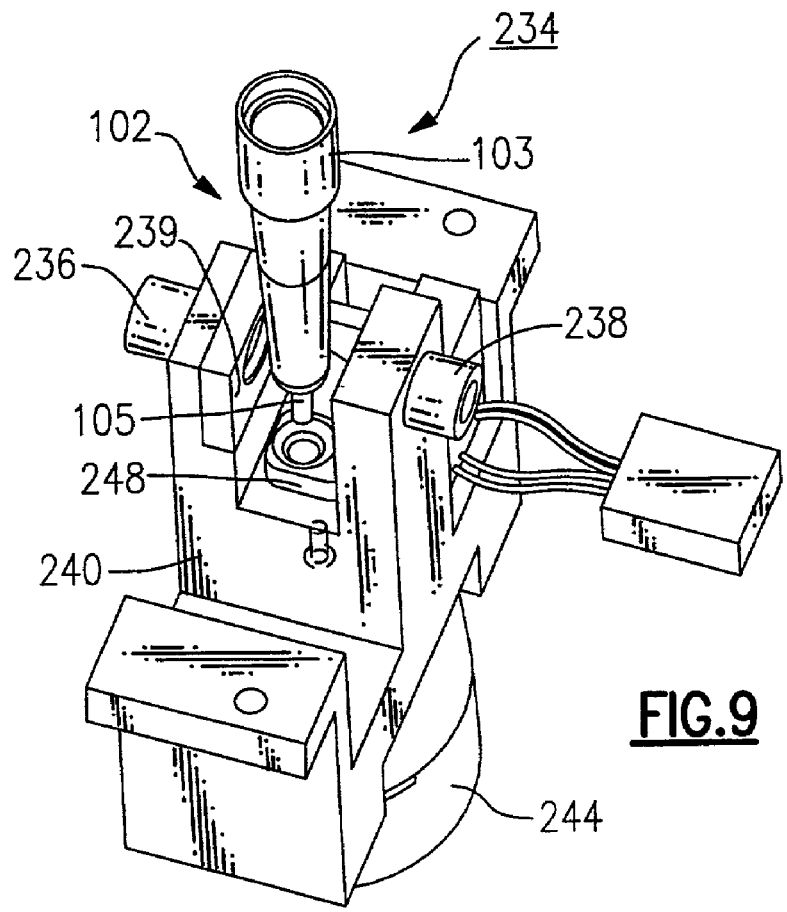
FIGS. 9 and 10 are partial side elevational views illustrating an sample integrity read station in accordance with one embodiment of the invention for the auxiliary sample handler of FIGS. 1-8.
Figure 10:
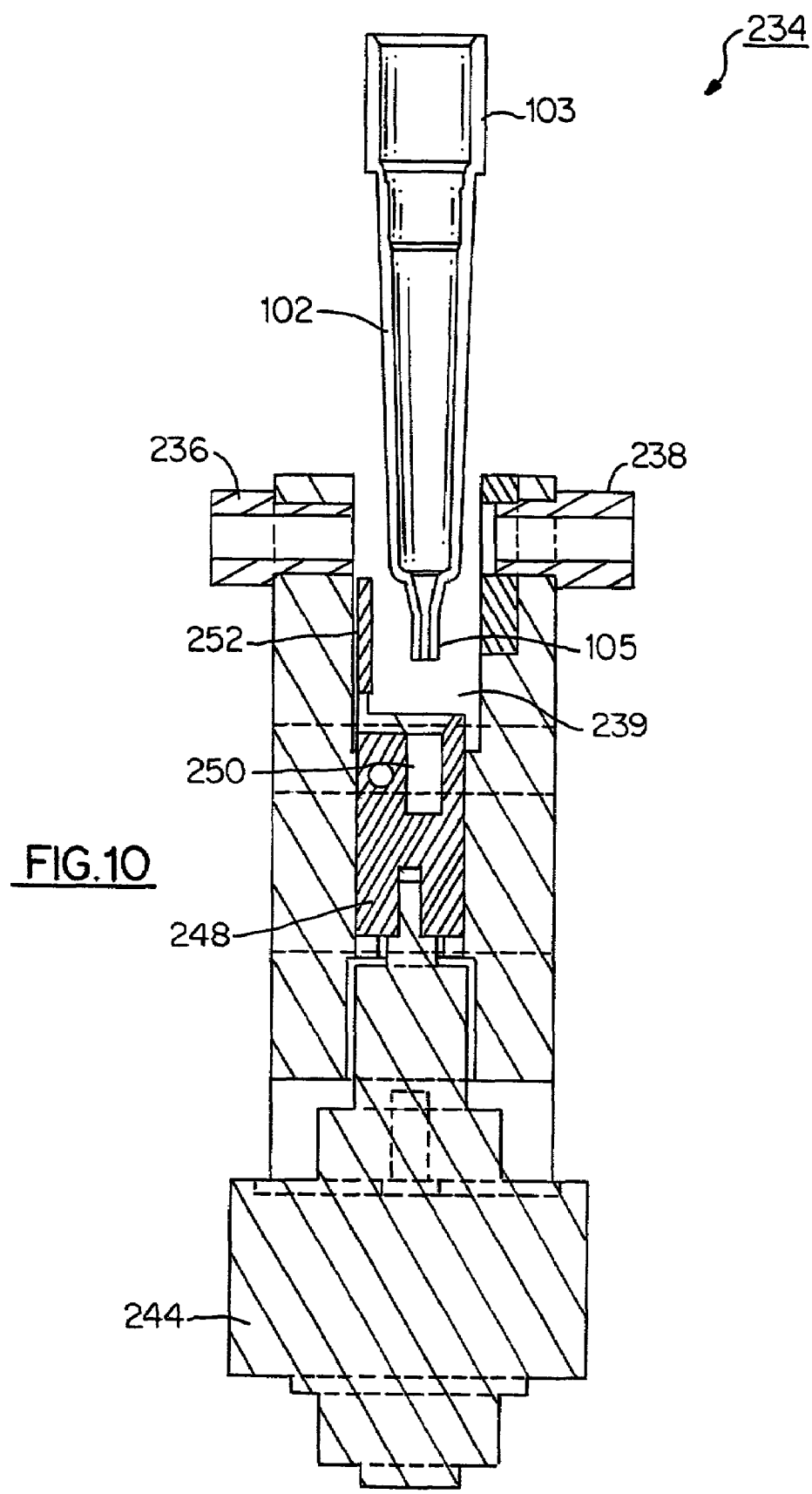

Still referring to FIGS. 2, 3, 5 and 8, each of the tip supply stations 118 of the support ring 114 of the outer rotor assembly 92 are circular openings which are sized to receive a metering tip 102, FIGS. 9, 10, from a tip supply (not shown) at a tip deposit station 150 provided as an opening in an adjacent cover 166 covering the drive motor (not shown) for the rotatable support ring 114 of the outer rotor assembly 92.

According to this embodiment, a total of sixty (60) equally spaced tip supply stations 118 are provided, though it should be apparent, as previously noted above, that this parameter can be suitably varied.

According to this specific embodiment, each of the sample container supply stations 100 and the tip supply stations 118 of the inner rotor and outer rotor assemblies 88, 92, respectively, are sized to receive a fluid aspirating/dispensing member. According to this embodiment, the fluid aspirating/dispensing member is a metering tip 102, shown in FIGS. 9 and 10, which includes an open upper end 103 and a lower dispense end 105 through which liquid can be dispensed. More specifically, the metering tip described herein is a disposable plastic member manufactured by the Johnson & Johnson Company under the trade name of Vitros™, though it will be apparent that other fluid dispensing/aspirating members can be substituted.

Referring to FIGS. 2-6, the auxiliary sample handler 40 includes a tip sealer 142 which is mounted by conventional means, such as threaded fasteners, to the exterior of the housing 80.

Figure 6:
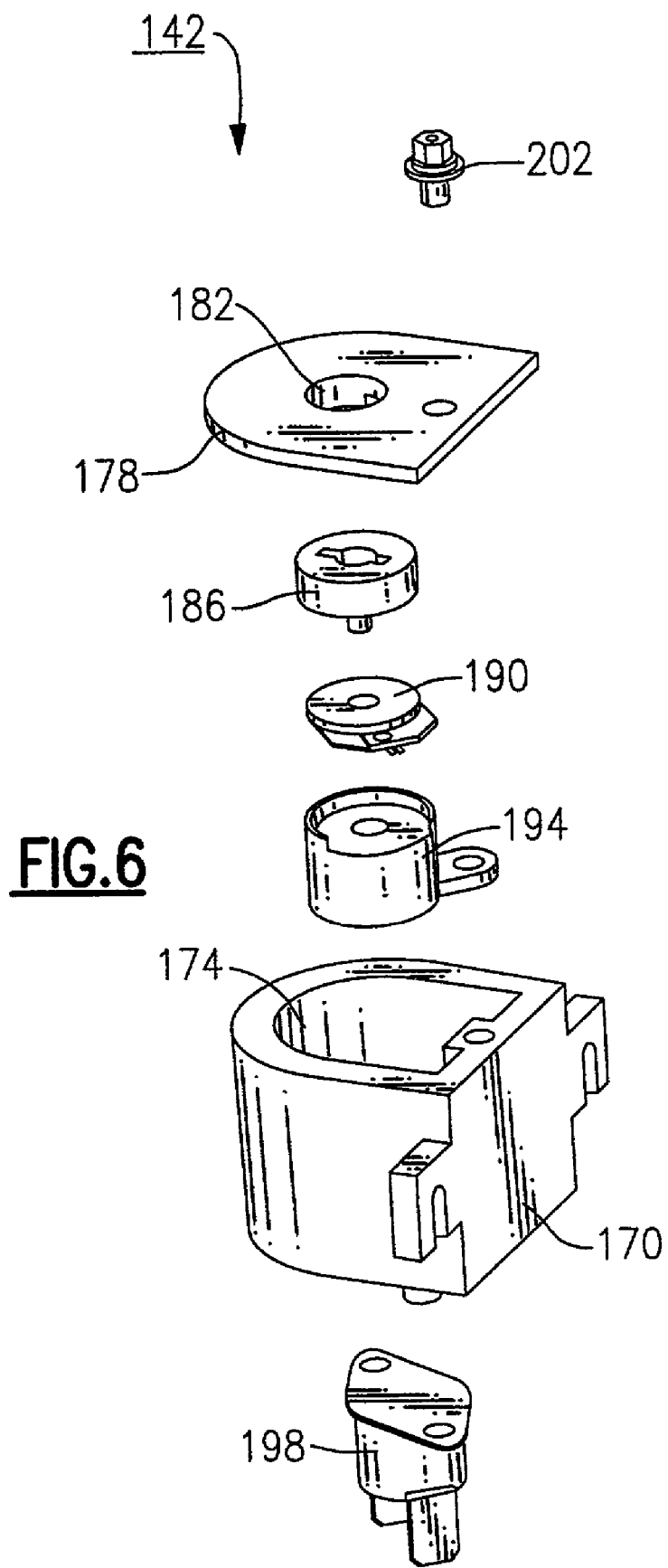
FIG. 6 is an exploded top perspective view of a tip sealer used in connection with the auxiliary sample handler of FIGS. 1-5.

Referring more particularly to FIG. 6, the tip sealer 142 includes a housing 170 which is mounted to the exterior of the handler housing 80, FIG. 3, the housing having a defined interior 174 and a cover 178 which covers the top end of the housing. A number of components are contained within the sealer housing 170 including a cylindrical support 194, and a heating element assembly 190, which is placed in a recess of the support within a bottom portion of an anvil 186. The heating element assembly 190 includes a resistive type heater and a control thermistor. The cover 178 includes a center opening 182 which is sized to permit passage of a metering tip 102, FIG. 9, such that the opening of the dispense end 105 of the tip can be sealed through engagement with the heated anvil 186. A safety thermostat 198 attached to the bottom of the housing 170 automatically shuts down the tip sealer 142 if a predetermined temperature is reached to prevent overheating. Further details relating to the sealing of metering tips in this manner is described in commonly owned U.S. patent application Ser. No. 09/658,356 to Jacobs et al., entitled ANALYZER WITH SAMPLE QUALITY MEASUREMENT, AND METHOD, the entire contents of which are incorporated herein by reference.

Figure 7:
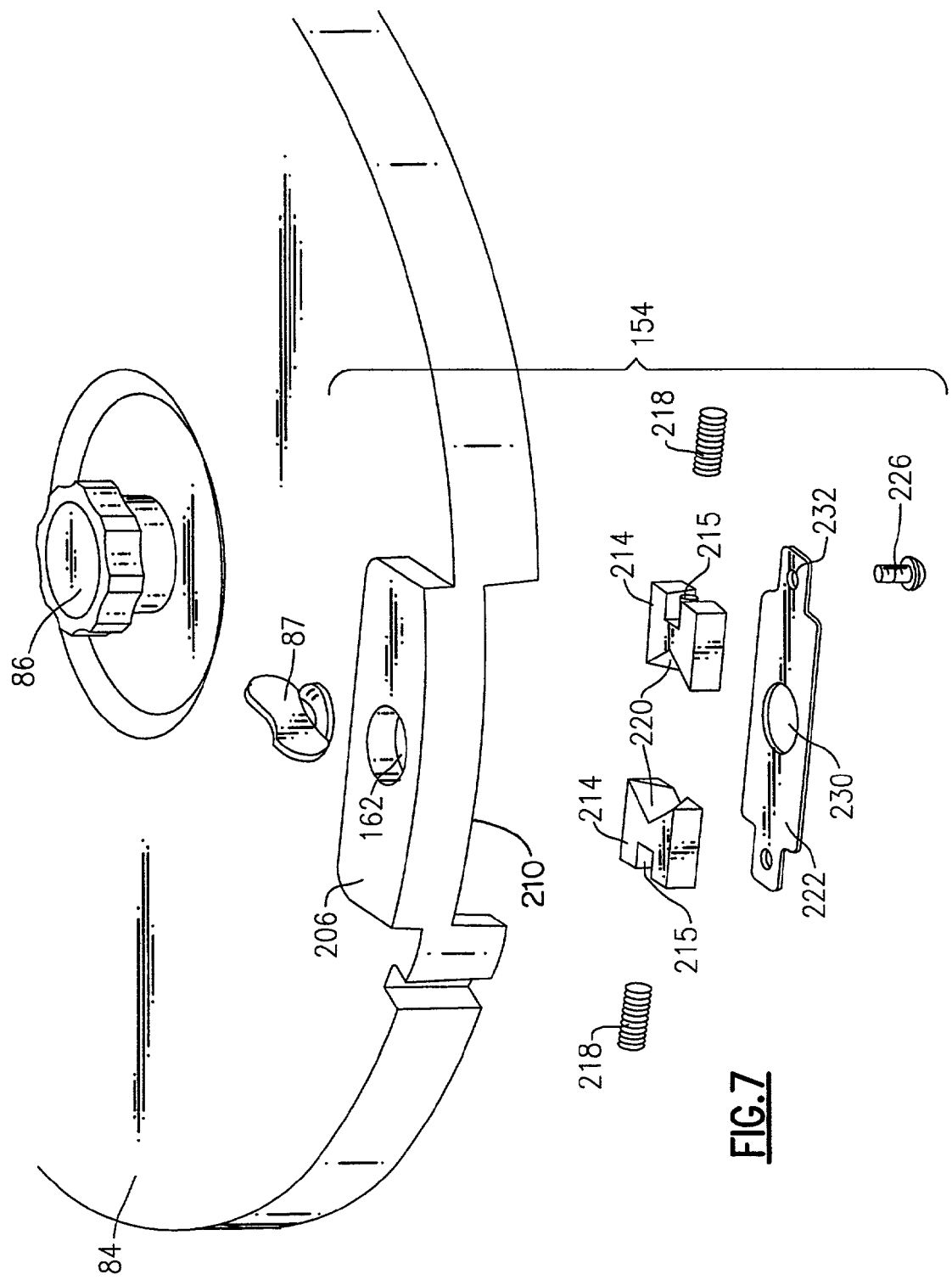
FIG. 7 is a partial top perspective of the cover of the auxiliary sample handler of FIGS. 1-6 showing an exploded view of a tip stripper.

Referring to FIG. 7, the auxiliary sample handler 40 further includes a tip stripping assembly 154 that is provided within a recessed portion 210 of the bottom of the cover 84. A pair of V-blocks 214 are biasedly maintained in a first or "home" position by a pair of compression springs 218 within respective slotted regions 215. The V-blocks 214 are biased in order to create a predetermined gap between a pair of tapered surfaces 220. The cover 84 includes an opening 162 within a raised portion 206, which is aligned with the gap of the V-blocks 214 to permit passage there through of a metering tip 102, FIG. 9. A retaining plate 222 used to support the components of the tip stripping assembly 154 is secured to the bottom of the cover 84 using fasteners 226 (only one being shown in FIG. 7) which extend through corresponding holes 232 formed in the retaining plate.

Referring to FIGS. 9 and 10, a sample integrity read station 234 includes a station housing 240 and an optical reading device, such as a spectrophotometer which includes receiving and transmitting optics 236, 238 disposed on opposite sides of a test slot or cavity 239. A linear actuator 244 is disposed at the bottom of the station housing 240, the actuator having an engagement member 248 attached thereto which is vertically movable and includes a tip receiving cavity 250 and a vertically extending flag 252, according to this embodiment. The actuator 244 and engagement member 248 together form a lift mechanism that aligns the fluid contents of a retained metering tip 102 with the receiving and transmitting optics 236, 238 of the spectrophotometer. The housing 240 of the sample integrity read station 234 is stationary positioned to the mounting plate 138 beneath a predetermined angular position of the circular ring 96 and the cavity 239 is aligned with the sample container supply stations 100, FIG. 5. As described below, the sample integrity received station 234 is provided to provide spectrophotometric analysis of the sample contents of a sealed metering tip 102 in order to ascertain the presence of certain sera components, such as hemoglobin, albumin, lipoproteins, glucose, and others.

As will now be more clearly described, the above-described auxiliary sample handler 40 is used to asynchronously link the dry chemistry and wet chemistry systems of the combinational clinical analyzer 10. Having completed the description of the individual features and subassemblies of the auxiliary sample handler 40, details relating to the operation of the sample handler in terms of the analyzer 10 is now provided.

Initially, a plurality of unsealed metering tips 102 are loaded one at a time as fed from a tip supply (not shown) through the opening that defines the tip deposit station 150 and are dropped into empty tip supply stations 118 provided on the support ring 114 of the outer rotor assembly 92. The support ring 114 is rotated incrementally by means of the gear drive mechanism (not shown) in order to align empty tip supply stations 118 into proper alignment with the tip deposit station 150.

As previously noted, the primary sample handler 14 contains a plurality of patient sample containers 18 which are movably disposed on a carousel. Details relating to the primary sample handler 14 and movement of the sample containers 18 are commonly known to those of ordinary skill in the field and do not form an essential part of the invention. As noted above, the metering transport rail 26 is aligned with the primary sample handler 14 and the auxiliary sample handler 40 such that a metering tip 102, FIG. 9, can be attached onto a proboscis (not shown) of the movable metering truck 30 of the primary metering mechanism 22 from a predetermined tip supply station 118.

The metering truck 30 is then shuttled along the transport rail 26 to the primary sample handler 14 and a volume of sample is drawn under vacuum and is aspirated from one of the patient sample containers 18 into the metering tip 102, FIGS. 9 and 10. Specific details relating to the attachment of a metering tip to a proboscis as well as details relating to the aspiration and metering of sample and other fluids are commonly known to those in the field. An example is provided, for example, in U.S. Pat. No. 4,340,390 to Collins et al., the entire contents of which are herein incorporated by reference.

The metering truck 30 carrying the unsealed metering tip 102 with aspirated sample is then shuttled along the transport rail 26 from the primary sample handler 14 to the metering station 68. At the metering station 68, a volumetric portion of patient sample contained within the metering tip 102 is dispensed onto a dry slide element, shown pictorially as 36 in FIG. 1, which is arranged to be loaded using conventional means, such as a reciprocating pusher blade 39, also shown pictorially in FIG. 1, into the first incubator assembly 34. The sample which is metered is then used in conjunction with the dry chemistry system of the herein described combinational analyzer 10. The sample is metered onto, for example, a calorimetric or potentiometric slide element which is incubated, the sample being analyzed at a read station for correlated analyte detection. Details relating to the incubation and testing of dry slide elements is known in the field such as described, for example, in U.S. Pat. No. 4,296,069 entitled: Apparatus for Processing an Analysis Slide, and therefore require no further discussion.

Following the above-described metering step, the metering tip 102 is then further shuttled by the metering truck 30 toward the auxiliary sample handler 40 and more specifically to the tip sealer 142. At the tip sealer 142, the metering tip 102 is placed within the opening 182 of the sealer housing 174 and is lowered until the tip is positioned relative to the anvil 186. Heat from the heating element 190 is applied through the anvil 186 to the dispense end 105 of the tip 102 while the tip is still attached to the proboscis (not shown) of the metering truck 30. The fluid within the tip 102 is aspirated further away from the dispense end 105 and a bubble is formed which prevents temperature effects to the fluid as well as removing the fluid from the area to be sealed. As noted above, further details relating to the above noted sealing operation are provided in previously incorporated U.S. patent application Ser. No. 09/658,356 entitled: ANALYZER WITH SAMPLE QUALITY MEASUREMENT, AND METHOD.

The above sealing operation seals the dispense end 105 of the metering tip 102, FIGS. 9, 10, and therefore creates a sample supply container for use by the wet chemistry system of the present combinational analyzer 10 as will be described below.

Following the above sealing steps, the proboscis (not shown) is raised in a conventional manner, removing the metering tip 102 from the tip sealer 142. The metering tip 102 is then shuttled along the transport rail 26 by the metering truck 30 to the tip stripping assembly 154 which is provided on the cover 84 of the auxiliary sample handler 40. The opening 162 of the tip stripping assembly 154 is aligned with the transport rail 26 and more specifically the travel path of the metering truck 30. The proboscis (not shown) is lowered along with the attached metering tip 102, FIG. 9, into the opening 162 of the raised portion 206 of the cover 84. Initially, the dispense end 105 of the sealed metering tip 102, FIGS. 9, 10, engages the ramped surfaces 220 of the V-blocks 214. As the proboscis is further lowered, the downward force applied by the tip 102 against the ramped surfaces 220 causes the gap between the V-blocks to widen and permits the entire metering tip 102 to pass through the extended gap. When the top of the upper end 103 of the metering tip 102 has passed through the V-blocks 214, the V-blocks are caused to close inwardly due to the biasing force applied by each of the compression springs 218 toward the body of the proboscis, above the top of the metering tip 102. Upward movement of the proboscis therefore causes engagement against the shoulder of the open upper end 103 of the metering tip 102, causing the tip to be stripped from the proboscis and dropped into an empty sample container supply position 100 of the circular ring 96 of the inner rotor assembly 88.

A tip presence sensor located at a dump position of the auxiliary sample handler 40 indicates whether or not a sample container supply station 100 is empty prior to loading the sealed metering tip 102, the sensor further confirming the presence of a new tip which has been loaded.

The above noted steps are repeated in order that a plurality of sealed metering tips 102 are individually added to the auxiliary sample handler 40 and more specifically to sample container supply stations 100 of the inner rotor assembly 88. The rotatable ring 96 of the inner rotor assembly 88 is driven about its axis of rotation through means of the meshing of the engagement portion 130 of the drive motor and the gear teeth 134 provided on the ring 96 either incrementally or as required. The retained sample containers (sealed metering tips 102) are driven relative to an aspiration station 158 and sample integrity read station 234. According to the present embodiment, the sample integrity read station is angularly disposed between the tip stripping assembly 154 and the aspiration station 158. The locations of each of the above stations 158, 234 can of course be suitably varied. What should be noted is that the disposition of the sample integrity station 234 within the housing of the auxiliary sample handler 40 permits readings to be performed at a time which does not affect throughput of the analyzer 10.

As more clearly shown in FIGS. 9 and 10, a sealed metering tip 102 is advanced by the inner rotor assembly 88, FIG. 3, to the sample integrity station 234. As noted previously, the sample integrity read station 234 is placed at a predetermined circumferential position relative to the sample container supply positions 100 of the rotatable ring 96. At this station 234 and according to his embodiment, the sealed metering tip 102 is roughly angularly aligned with the test cavity 239 and moreover is roughly vertically aligned with the receiving and transmitting optics 236, 238 of the optical testing device in the position which is shown in FIG. 10.

The optical reading apparatus according to this embodiment, is a spectrophotometer which makes light absorbance transmission measurements of a sample retained within the sealed disposable metering tip 102. The sealed metering tip 102, being made from a transparent plastic material therefore permits optical testing to be performed upon the fluid contents. Details relating to the optical reading of the fluid contents of the sample are known as provided in U.S. Pat. Nos. 6,013,528 and 5,846,492, to Jacobs et al., the entire contents of each being hereby incorporated by reference.

According to this embodiment, the lift mechanism is used to better or repeatably align each sealed metering tip 102 to the receiving and transmitting optics 236, 238 of the optical testing apparatus. The actuator 244 is initially engaged and the tip receiving cavity 250 of the engagement member 248 of the linear actuator 244, sized to receive the dispense end 105 of the tip 102, causes the tip to be moved upwardly relative to its position within the ring 96 (the ring is not shown in FIGS. 9 and 10). The upward movement of the sealed metering tip places the lower portion of the tip containing the aliquot of sample fluid into proper alignment between the receiving and transmitting portions 236, 238 of the optical testing device prior to obtaining readings of the contained aliquot sample. The flag 252 provided on the engagement member 248 is used to perform a dark read of the optical reading apparatus prior to lifting the metering tip 102, as better described by the above incorporated Jacobs patents.

Upon completion of the read, the engagement member 248 is lowered and the metering tip is again lowered into engagement within the outer slotted opening 104 of the corresponding sample container supply position 100. The ring 96 of the inner rotor assembly 88 resumes rotational movement by means of its gear drive mechanism until the metering tip 102 is aligned with the opening representing the aspiration station 158. If sample is required, the secondary metering system 42 is used to bring a micro-tip (not shown) from the micro-tip loader 58 using a proboscis (not shown) extending downwardly from the movable metering truck 44 which is moved into position using the metering transport rail 26. The operation of the secondary metering mechanism in terms of the attachment of a tip to the proboscis (not shown), the raising and lowering of the proboscis relative to the metering truck 44, the movement of the metering truck along the transport rail 26 and the aspiration and dispensing of fluid using the micro-tip are literally identical to that of the primary metering mechanism 22, FIG. 1 and those details in and of themselves require no further discussion. As previously defined, however, the micro-tip is a fluid dispensing member which can fit within the confines of a sealed metering tip 102.

The micro-tip is positioned within the confines of the sealed metering tip 102 in order to aspirate a predetermined volume of liquid from the sealed tip to use the liquid to conduct a wet assay or dilution. The metering truck 44 then moves the micro tip into alignment with a reaction vessel 64 and dispenses the aspirated fluid. Following the delivery of patient sample aspirated from the secondary sample container, the micro tip is disposed of by dropping the used micro-tip into a dump station (not shown) of the analyzer 10.

According to this embodiment, separate liquids, such as at least one reagent fluid, are also brought to the reaction vessel 64, from the reagent wheel 52 using a separate metering tip 102, FIG. 9 which aspirates fluid from a container disposed within the reaction wheel and dispenses the reagent fluid as needed. For example, reagent (s) can be aspirated using a tip 102 which is obtained by the secondary metering mechanism 42 from the outer rotor assembly 92. Preferably, the coordination of wet assay testing utilizes the auxiliary sample handler 40 as part of the scheduling in order to effectively utilize throughput. Details relating to the operation of the wet chemistry portion of the herein described analyzer are provided in concurrently filed U.S. Ser. No. 60/306,830 entitled: Chemistry System for a Clinical Analyzer to Jakubowicz et al., the entire contents of which are herein incorporated.

Once the sealed metering tip 102 has been used in accordance with all tests/assays which may be required based on the scheduling of the combinational analyzer 10, the ring 96 of the inner rotor assembly 88 is rotated into alignment with the tip removal assembly 122. At this location, an actuable hook blade 124 which is moved outwardly by the assembly engages the protruding upper end 103 and body of the metering tip 102 and pulls the tip from the slotted outer opening 104 of the supply station 100 to the larger diameter inner opening 108. The inner opening 108 of the sample container supply stations 100 has a diameter which is larger than that of the upper end 103 of the tapered metering tip 102, thereby causing the tip to fall through the opening and into a dump station (not shown) located beneath the ring 96. A position sensor 128 detects the position of the hook blade relative to the inner rotor assembly 88.

| PARTS LIST FOR FIGS. 1-10 |
| --- |
| 10 analyzer |
| 14 primary sample handler |
| 18 sample containers |
| 22 primary metering mechanism |
| 26 metering transport rail |
| 30 metering truck |
| 34 first incubator assembly |
| 36 slide element |
| 39 pusher blade |
| 40 auxiliary sample handler |
| 42 secondary metering mechanism |
| 44 metering truck |
| 52 reagent wheel |
| 56 second incubator assembly |
| 58 micro-tip loader |
| 60 reaction vessel conveyor |
| 64 reaction vessel |
| 68 metering station |
| 80 housing |
| 84 cover |
| 86 handle |
| 87 twist fasteners |
| 88 inner rotor assembly |

-continued

PARTS LIST FOR FIGS. 1-10

- 90 stanchions
- 92 outer rotor assembly
- 96 circular ring member
- 100 sample container supply stations
- 102 metering tip
- 103 open upper end
- 104 outer slotted opening
- 105 tapered lower dispense end
- 108 inner opening
- 114 support ring
- 118 tip supply stations
- 120 slots
- 122 tip removal assembly
- 124 hook blade
- 126 position sensor
- 128 position sensor
- 130 engagement portion of drive motor
- 134 edge teeth-inner ring
- 138 mounting plate
- 142 tip sealer
- 146 edge teeth-outer ring
- 150 tip deposit station
- 154 tip stripping assembly
- 158 aspiration station
- 166 cover
- 170 housing
- 174 opening
- 178 cover
- 182 opening
- 186 anvil
- 190 heating element assembly
- 194 support
- 198 safety thermostat
- 206 raised portion
- 210 recessed portion
- 214 V-blocks
- 215 slotted portions
- 218 springs
- 220 tapered surfaces
- 222 retaining plate
- 226 fastener
- 230 opening
- 232 hole
- 234 sample integrity read station
- 236 transmitting optics
- 238 receiving optics
- 239 test slot or cavity
- 240 housing
- 244 linear actuator
- 248 engagement member
- 250 tip receiving cavity
- 252 flag It will be apparent that other modifications and variations are possible which employ the inventive concepts of the present invention. For example, the above described auxiliary sample handler can be used in connection with a combinational analyzer having multiple chemistry stations or the handler can include additional aspiration stations, for example, to permit dilution of an assay of a dry chemistry system.

We claim:

1. An auxiliary sample handler for retaining a plurality of auxiliary patient sample containers, said auxiliary sample handler comprising:

a housing that includes a plurality of tip retaining stations;

a housing cover sized to cover each of said tip retaining stations;

a drive mechanism used to rotate said tip retaining stations about an axis of rotation;

a plurality of metering tips, each of said metering tips retaining a quantity of sample liquid from a primary sample handler of a clinical analyzer and therein acting as an auxiliary sample container, each of said metering tips including a dispense end;

a sealing mechanism disposed on said housing for sealing the dispense end of each of said metering tips containing sample liquid to form a plurality of sealed metering tips;

a tip stripping mechanism disposed in said housing cover for sequentially removing each said sealed metering tip from a metering mechanism of a clinical analyzer and into one of said plurality of tip retaining stations; and an aspiration station including an opening in said housing cover to permit selective access to at least one said sealed metering tip in order to permit aspiration therefrom, said drive mechanism being configured to rotate said tip retaining stations into position with said aspiration station.

2. The auxiliary sample handler as recited in claim 1, wherein said sealing mechanism includes at least one heated element.

3. The auxiliary sample handler as recited in claim 1, including an optical instrument disposed in said housing for measuring at least one optical property of sample liquid contained in each of said plurality of metering tips, said drive mechanism being configured to selectively move each of said tip retaining stations in relation to said optical instrument.

4. The auxiliary sample handler as recited in claim 3, wherein said optical instrument is a spectrophotometer.

5. The auxiliary sample handler as recited in claim 1, wherein said plurality of tip retaining stations are disposed on a ring.

6. The auxiliary sample handler as recited in claim 5, including a second ring having a plurality of tip retaining stations disposed thereupon.

7. The auxiliary sample handler as recited in claim 6, wherein said first ring and said second ring are concentric.

8. The auxiliary sample handler as recited in claim 7, wherein each of said first and second rings is independently driven about a common axis of rotation.

9. The auxiliary sample handler as recited in claim 8, wherein each of said rings is bi-directionally rotatable about said common axis of rotation.

10. The auxiliary sample handler as recited in claim 1, including a detection mechanism to detect when any tip retaining station of said auxiliary sample handler is empty.

11. The auxiliary sample handler as recited in claim 1, including a removal mechanism to remove sealed metering tips from said tip retaining station when testing is completed.

* * * * *